(12) United States Patent
Bettenga

(10) Patent No.: US 11,571,202 B2
(45) Date of Patent: Feb. 7, 2023

(54) DEVICES AND METHODS FOR TISSUE GRAFT FIXATION IN GLENOHUMERAL INSTABILITY REPAIR

(71) Applicant: Smith & Nephew, Inc., Memphis, TN (US)

(72) Inventor: Mason Bettenga, Memphis, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 181 days.

(21) Appl. No.: 17/238,676

(22) Filed: Apr. 23, 2021

(65) Prior Publication Data

US 2021/0236114 A1 Aug. 5, 2021

Related U.S. Application Data

(62) Division of application No. 16/309,658, filed as application No. PCT/US2017/034787 on May 26, 2017, now Pat. No. 10,987,097.

(60) Provisional application No. 62/350,756, filed on Jun. 16, 2016.

(51) Int. Cl.
*A61B 17/04* (2006.01)
*A61B 17/68* (2006.01)
*A61F 2/28* (2006.01)
*A61F 2/30* (2006.01)
*A61F 2/40* (2006.01)

(52) U.S. Cl.
CPC ........ *A61B 17/0401* (2013.01); *A61B 17/683* (2013.01); *A61F 2/2846* (2013.01); *A61F 2/30749* (2013.01); *A61F 2/4081* (2013.01); *A61B 2017/0403* (2013.01); *A61B 2017/0404* (2013.01); *A61B 2017/0408* (2013.01); *A61B 2017/0414* (2013.01); *A61B 2017/0417* (2013.01); *A61B 2017/0459* (2013.01); *A61F 2002/2835* (2013.01)

(58) Field of Classification Search
CPC ........ A61B 17/0401; A61B 2017/0403; A61B 2017/0404; A61B 2017/0408; A61B 2017/0417; A61B 2017/0459; A61F 2/0811; A61F 2002/0823; A61F 2002/0847; A61F 2002/0852; A61F 2002/2835
See application file for complete search history.

(56) References Cited

U.S. PATENT DOCUMENTS

| | | | |
|---|---|---|---|
| 10,499,900 B2 * | 12/2019 | Wade | A61B 17/0401 |
| 10,987,097 B2 * | 4/2021 | Bettenga | A61F 2/2846 |
| 2003/0167062 A1 * | 9/2003 | Gambale | A61B 17/0487 606/148 |
| 2007/0049970 A1 * | 3/2007 | Belef | A61B 17/0057 606/232 |
| 2013/0079820 A1 * | 3/2013 | Stanley | A61B 17/0401 606/232 |

(Continued)

*Primary Examiner* — Eric S Gibson
(74) *Attorney, Agent, or Firm* — Burns & Levinson, LLP; Joseph M. Maraia

(57) ABSTRACT

A surgical fastener comprising a generally flat, circular body and a generally cylindrical post fixedly coupled to a center of the body extending perpendicular to the body. Both of the body and the post include through holes configured for passage of a suture. A length of the post is selected to extend through both of a bone graft and at least a portion of bone for providing shear and/or anti-rotational support to the surgical fastener across a fracture line in the bone.

10 Claims, 9 Drawing Sheets

(56) References Cited

U.S. PATENT DOCUMENTS

| | | | | |
|---|---|---|---|---|
| 2014/0277185 A1* | 9/2014 | Boileau | .............. | A61B 17/1659 606/86 R |
| 2015/0272567 A1* | 10/2015 | Feezor | ............... | A61B 17/0401 606/232 |
| 2015/0359530 A1* | 12/2015 | Moore | ............... | A61B 17/0401 606/232 |
| 2016/0089131 A1* | 3/2016 | Wade | ..................... | A61B 17/84 606/232 |
| 2017/0071592 A1* | 3/2017 | Feezor | ............... | A61B 17/0485 |
| 2017/0112554 A1* | 4/2017 | Zadeh | ................ | A61B 17/0401 |
| 2017/0112625 A1* | 4/2017 | Taverna | ..................... | A61F 2/40 |
| 2017/0231615 A1* | 8/2017 | Tang | .................. | A61B 17/0401 606/232 |
| 2019/0076139 A1* | 3/2019 | Dreyfuss | ............... | A61F 2/0811 |
| 2019/0307568 A1* | 10/2019 | Bettenga | ............... | A61B 17/683 |
| 2020/0038010 A1* | 2/2020 | Zakhary | ............. | A61B 17/7053 |
| 2020/0178953 A1* | 6/2020 | Da Silva | ............ | A61B 17/0482 |
| 2020/0306047 A1* | 10/2020 | Boileau | ................. | A61F 2/2846 |
| 2021/0236114 A1* | 8/2021 | Bettenga | .............. | A61B 17/683 |

\* cited by examiner

DEVICES AND METHODS FOR TISSUE GRAFT FIXATION IN GLENOHUMERAL INSTABILITY REPAIR

CROSS-REFERENCE TO RELATED APPLICATIONS

This application is a divisional of U.S. application Ser. No. 16/309,658, filed Dec. 13, 2018, entitled DEVICES AND METHODS FOR TISSUE GRAFT FIXATION IN GLENOHUMERAL INSTABILITY REPAIR, which in turn is the U.S. national phase entry under 35 U.S.C. § 371 of International Application No. PCT/US2017/034787, filed May 26, 2017, which in turn claims priority to and benefit of U.S. Provisional Application No. 62/350,756, filed Jun. 16, 2016, the contents of which are incorporated herein by reference in their entirety for all purposes.

BACKGROUND

The shoulder joint, also referred to as the glenohumeral joint, is the joint between the glenoid cavity (a part of the scapula) and the head of the humerus (upper arm bone). The glenoid cavity is shallow, covering only about a third of the head humeral head. As a result, the glenoid cavity provides relatively little bony constraint upon motion of the humerus and the glenohumeral joint exhibits the widest range of motion of all joints in the human body. While the glenohumeral joint is also constrained by soft tissue (e.g., cartilage attached to the rim of the glenoid cavity, tendons, etc.), soft tissue in general cannot provide the same degree of constraint as bone. Accordingly, it is relatively easy to force the humerus from its normal anatomical position with respect to the glenoid socket, that is, to dislocate the shoulder. While not life threatening, a dislocated shoulder can cause pain and immobilization of the joint, impacting a patient's lifestyle.

In the case of severe bone loss caused by shoulder instability and/or dislocation, a surgeon may perform a "Latarjet procedure" to make the repair. In a Latarjet procedure, a surgeon attempts to restore bone mass to the glenoid cavity by securing a bone graft to the surface of the glenoid suffering bone loss. The bone graft may or may not be attached to soft tissue. When successful, the bone graft acts as a scaffold, allowing the glenoid bone to grow into the bone graft and restore the lost glenoid bone mass.

During the Latarjet procedure, fixation devices, such as solid screws, may be used to provide compression when securing the graft to the bone. Alternatively, if suspension fixation is desired, the fixation devices may be in the form of a flat button that is positioned on a surface of the bone graft and/or bone and is tensioned in place by a suture. However, with suspension fixation, such flat button fixation devices provide very little shear stability across the fracture line compared to solid screws.

SUMMARY

Described herein is a fixation device that uses suspension fixation while incorporating a long post attached to a flat button. The long post is solid and provides a shear stability greater than or equal to a screw. When two or more fixation devices are used, the fixation devices also provide rotational stability of the bone graft with respect to the underlying bone. Advantageously, the fixation devices of this disclosure can also be passed through anatomical structures arthroscopically much easier than standard screws.

Further examples of the surgical fastener of this disclosure may include one or more of the following, in any suitable combination.

In examples, the surgical fastener of this disclosure includes a generally flat, circular body having a first surface and a second surface opposite the first surface and a generally cylindrical, solid post. The post has a first end, a second end, and a longitudinal axis extending between the first and second ends, the longitudinal axis being perpendicular to the second surface of the body. The first end of the post is fixedly coupled to a center of the second surface. A length of the post is selected to extend through a bone graft and a portion of bone.

In further examples, the body also includes a first through hole extending from the first surface to the second surface, the first through hole being located at the center of the second surface. In this example, the post further has a second through hole extending along the longitudinal axis from the first end to the second end, the second through hole in communication with the first through hole. The first and second through holes are configured for passage of a suture.

In other examples, the body further includes a pair of first through holes extending from the first surface to the second surface, the pair of first through holes being symmetrically offset from the center of the second surface. In this example, the post further has an eyelet at the second end of the post transverse to the longitudinal axis. The first pair of through holes and the eyelet are configured for the passage of a suture. In yet other examples, the length of the post is between about 20 mm and about 25 mm. A radius across the first surface of the body is about 7 mm. A diameter of the post is about 2.8 mm.

In examples, a method of tissue graft fixation of this disclosure includes: forming at least one axially aligned passage through a bone and a bone graft; passing a first portion of a suture through the passage, a second portion of the suture being coupled to a first fastener; positioning the first fastener against a surface of one of the bone graft or the bone by pulling the second portion of the suture through the passage until the second portion exits the passage; positioning a second fastener against the other of the bone graft or the bone by coupling the second fastener to the second portion of the suture; and adjusting the suture such that the first fastener and the second fastener apply pressure between the bone graft and the bone. In this example, one of the first fastener or the second fastener includes a generally flat, circular body and a generally cylindrical, solid post comprising a first end, a second end, and a longitudinal axis extending between the first and second ends. The longitudinal axis is perpendicular to the body, and the first end of the post is fixedly coupled to a center of the body. When the suture is adjusted, the post extends through the passage such that it extends through the bone graft and at least partially through the bone.

In further examples, the body also includes a first through hole extending from a first surface to an opposite second surface, the first through hole being located at the center of the body. In this example, the post further includes a second through hole extending along the longitudinal axis from the first end to the second end, the second through hole in communication with the first through hole. The first and second through holes are configured for passage of a suture.

In other examples, the body further includes a pair of first through holes extending from a first surface to an opposite second surface, the pair of first through holes being symmetrically offset from the center of the body. In this example, the post further has an eyelet at the second end of the post transverse to the longitudinal axis. The first pair of through holes and the eyelet are configured for the passage of a suture.

In yet further examples, a length of the post of the one of the first or second fasteners is between about 20 mm and about 25 mm. A diameter of the post of the one of the first or second fasteners is about 2.8 mm. A diameter of the at least one axially aligned passage is about 2.8 mm. The method further includes tying a surgical knot in the suture.

Examples of the tissue fixation construct of this disclosure include a first fastener and a second fastener coupled to the first fastener by a suture such that a distance between the first fastener and the second fastener can be adjusted by pulling on ends of the suture. One of the first fastener or the second fastener has a generally flat, circular body and a generally cylindrical, solid post having a first end, a second end, and a longitudinal axis extending between the first and second ends. The longitudinal axis is perpendicular to the body, and the first end of the post is fixedly coupled to a center of the body. A length of the post is selected to extend through a bone graft and a portion of bone.

In further examples, the body also includes a first through hole extending from a first surface to an opposite second surface, the first through hole being located at the center of the body. In this example, the post further has a second through hole extending along the longitudinal axis from the first end to the second end, the second through hole in communication with the first through hole. The first and second through holes are configured for passage of a suture.

In other examples, the body further includes a pair of first through holes extending from a first surface to an opposite second surface, the pair of first through holes being symmetrically offset from the center of the body. In this example, the post further has an eyelet at the second end of the post transverse to the longitudinal axis. The first pair of through holes and the eyelet configured are for the passage of a suture.

In yet further examples, a length of the post of the one of the first or second fasteners is between about 20 mm and about 25 mm. The other of the first or second fasteners includes a suture slidably coupled to the other of the first or second fasteners. The suture is in the form of a suture loop. The bone is a glenoid.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The disclosure will be more fully understood by reference to the detailed description, in conjunction with the following figures, wherein.

DETAILED DESCRIPTION

Figure 1A:
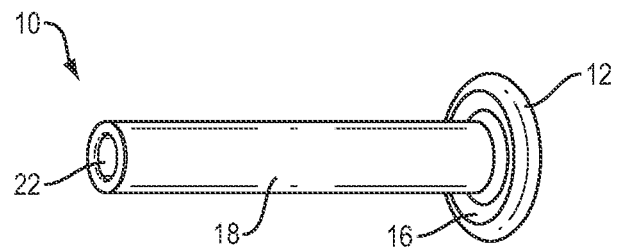
FIGS. 1A and 1B are illustrations of an example of the fixation device of this disclosure.

In the description that follows, like components have been given the same reference numerals, regardless of whether they are shown in different examples. To illustrate example(s) in a clear and concise manner, the drawings may not necessarily be to scale and certain features may be shown in somewhat schematic form. Features that are described and/or illustrated with respect to one example may be used in the same way or in a similar way in one or more other examples and/or in combination with or instead of the features of the other examples.

As used in the specification and claims, for the purposes of describing and defining the invention, the terms "about" and "substantially" are used represent the inherent degree of uncertainty that may be attributed to any quantitative comparison, value, measurement, or other representation. The terms "about" and "substantially" are also used herein to represent the degree by which a quantitative representation may vary from a stated reference without resulting in a change in the basic function of the subject matter at issue. "Comprise," "include," and/or plural forms of each are open ended and include the listed parts and can include additional parts that are not listed. "And/or" is open-ended and includes one or more of the listed parts and combinations of the listed parts.

Two examples of a fixation device 10, 30, according to the present disclosure, are illustrated in FIGS. 1A-B and 2A-B, respectively. In both examples, the fixation devices 10, 30 include a generally circular body 12 having a first surface 14, which may be flat or convex, for facing away from bone, and an opposite concave (or bowl-shaped) second surface 16, for facing bone. All edges of the body 12 are rounded to avoid chafing of a suture or graft. A radius across the first surface 14 of the body 12 may be about 7 mm. However, the radius may also be varied to accommodate a patient or procedure. The fixation device 10, 30 further includes a generally cylindrical, solid post 18 fixedly coupled to a center of the body 12 and extending perpendicular to the body 12. A length of the post 18 is selected to extend through both of a bone graft and a portion of bone, such as a glenoid bone. For example, the thickness of a bone graft may be about 5 mm to about 11 mm, while a length of the post 18 may be about 20 mm to about 25 mm, although the post 18 could be longer in some applications. Advantageously, as described in further detail below, the post 18 provides greater or equal shear support to the fixation device 10, 30 across the fracture line of the bone as compared to surgical screws. Furthermore, when two or more fixation devices 10, 30 are used, the fixation devices 10, 30 additionally provide rotational stability to the bone graft with respect to the underlying bone.

The body 12 and the post 18 can each be formed of surgical quality stainless steel. Other biocompatible materials are acceptable, such as a Delrin polymer available from Du Pont or a bioabsorbable material such as polylactic acid, polyglycolic acid disclosed in U.S. Pat. No. 3,739,773 (Schmitt et al.), or copolymers disclosed in U.S. Pat. No. 4,300,565 (Rosensaft et al.) and U.S. Pat. No. 4,429,080 (Casey et al.), all of which are incorporated herein by reference. A combination of absorbable and non-absorbable materials to form a partially absorbable fixation device can also be utilized. A polymer such as polylactic acid may be preferred for its slower absorption rate and therefore longer retention of structural integrity.

Figure 1B:
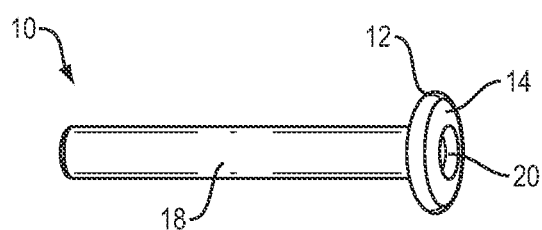

In the example of the fixation device 10 shown in FIGS. 1A-B, the body 12 further comprises a first through hole 20 extending from the first surface 14 to the second surface 16 of the body 12, the first through hole 20 being located at the center of the body 12. In this example, the post 18 also includes a second through hole 22 extending along the longitudinal axis of the post 18, the second through hole 22 being in communication with the first through hole 20. The first and second through holes 20, 22 are each configured for passage of a suture, as further described below. Diameters of the first and second through holes 20, 22 are variable and are selected based on the size of the suture to be used.

Figure 2A:
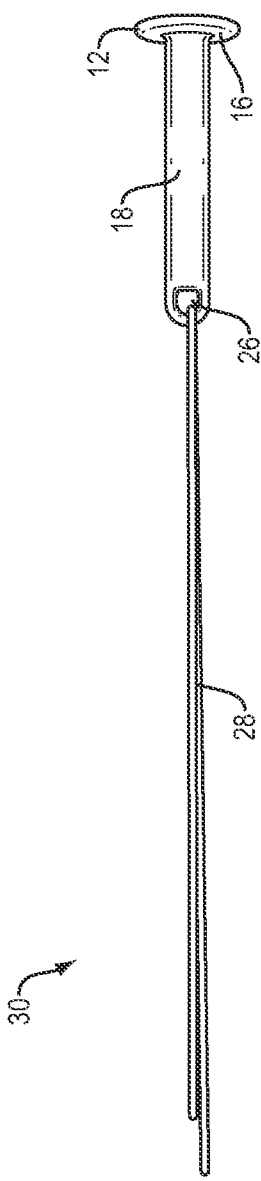
FIGS. 2A and 2B are illustrations of another example of the fixation device of this disclosure.
Figure 2B:
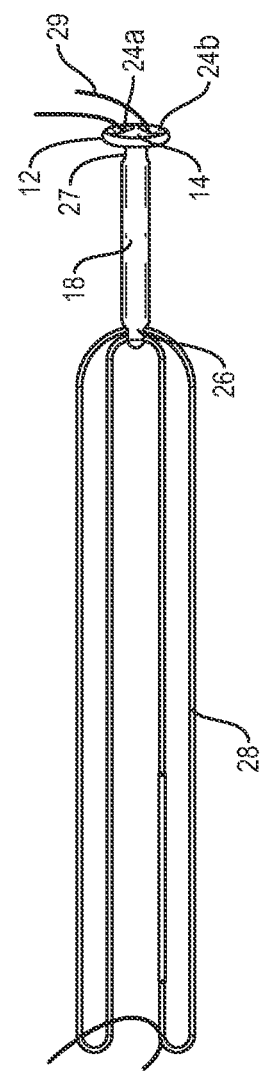

In the example of the fixation device 30 shown in FIGS. 2A-B, the body 12 further comprises a pair of first through holes 24a, 24b extending from the first surface 14 to the second surface 16 of the body 12. The pair of first through holes 24a, 24b are symmetrically offset from the center of the body 12 and are not obstructed by the post 18. The pair of first through holes 24a, 24b are configured for the passage of a suture, such as a lead or pull suture 29. In this example, the post 18 also includes an eyelet 26 extending through the distal end of the post 18 for passage of a suture. A tension suture 28 may be slidably coupled to the eyelet 26. The form of the tension suture 28 may be varied, in certain examples. For example, the tension suture 28 may be formed in a suture loop or bundle. In further examples, the tension suture 28 may be formed from a high-strength polyethylene or may be formed from metallic wire. In some examples, the post 18 also includes an eyelet 27 extending through the proximal end of the post 18 for passage of an additional suture, such as the pull suture 29. Sizes of the eyelets 26, 27 are variable, and are selected based on the size of the suture used.

Figure 3A:
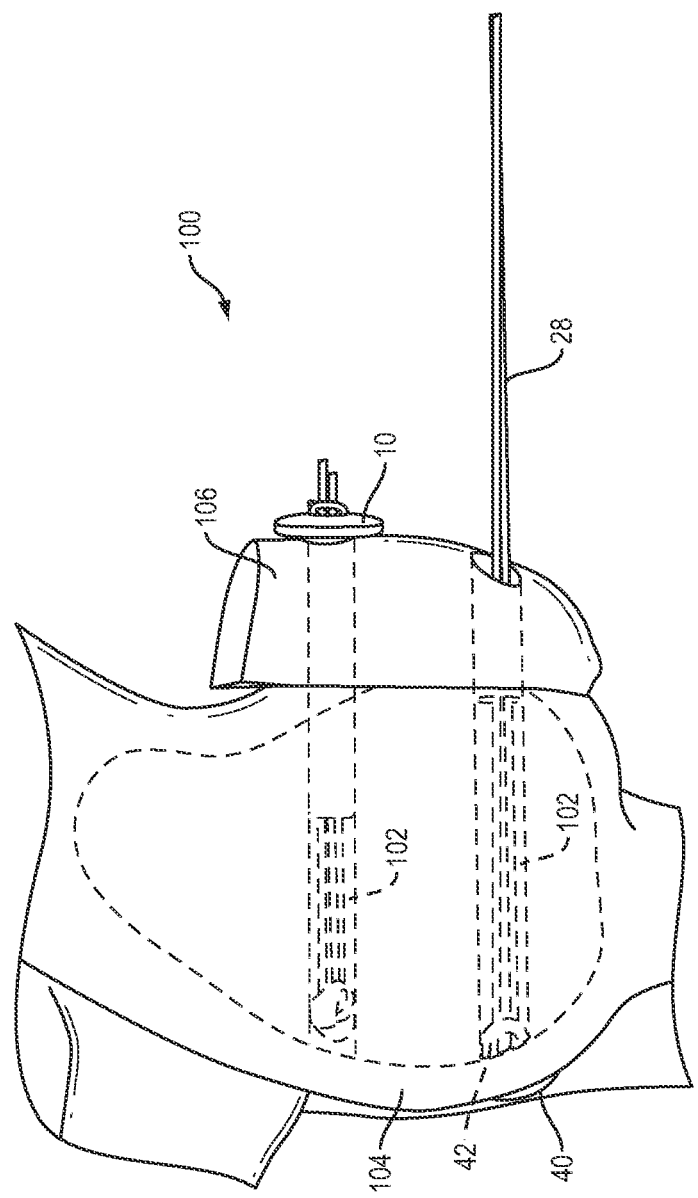
FIGS. 3A-C illustrate a method of graft fixation using the fixation device of FIGS. 1A and 1B.
Figure 3B:
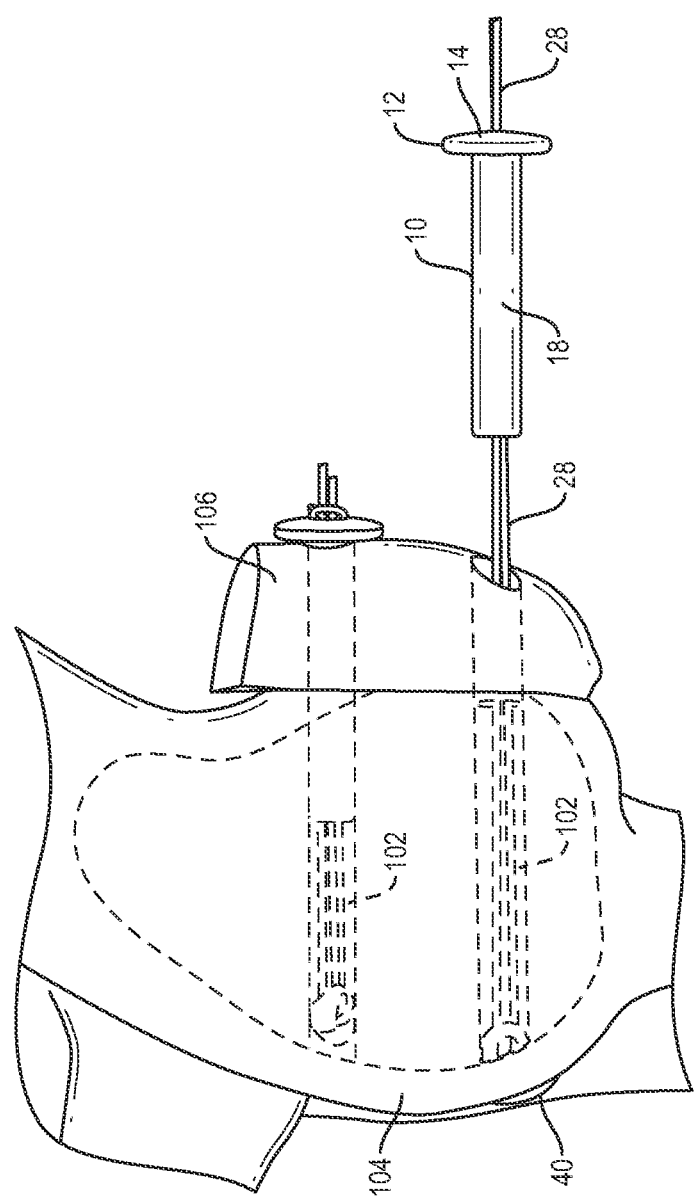
Figure 3C:
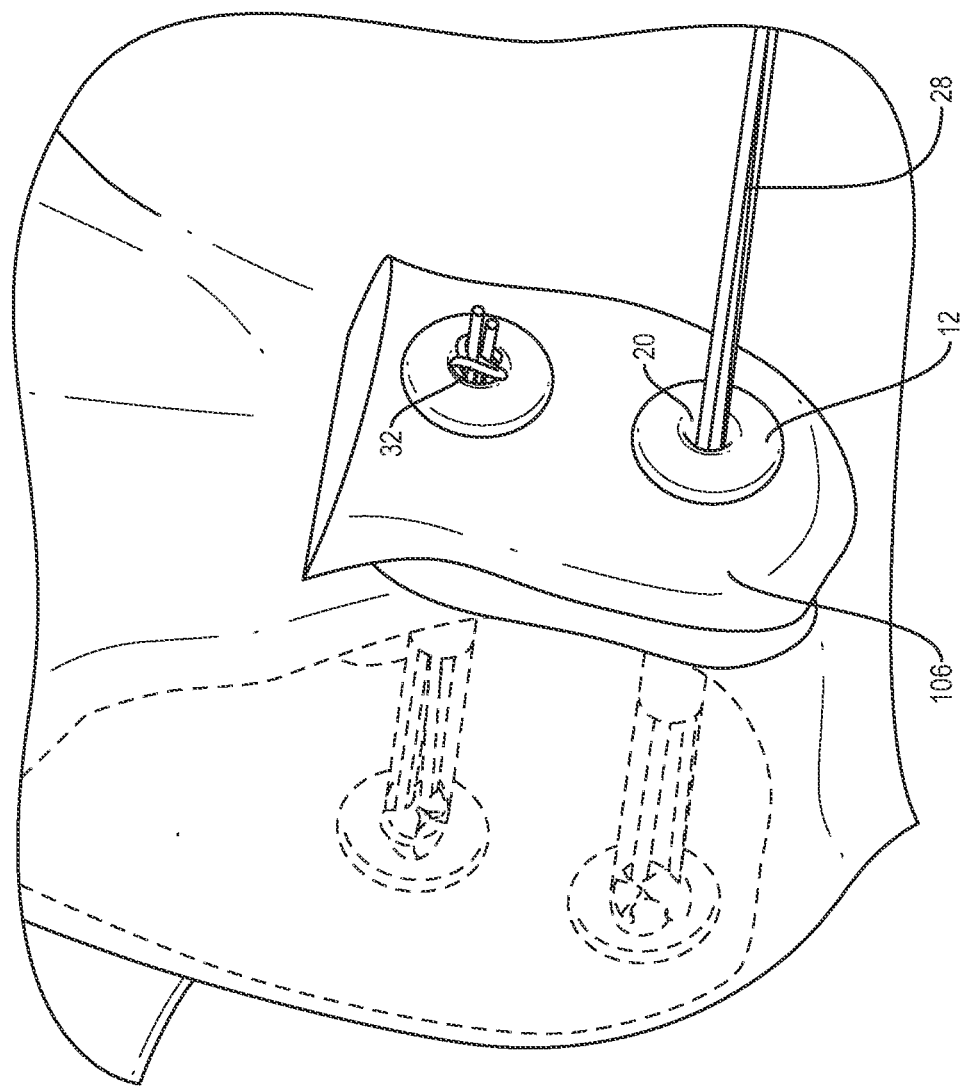

FIGS. 3A-C illustrate a method of bone graft fixation using fixation device 10 as described above. Referring to FIG. 3A, in which a shoulder 100 of a patient is illustrated, axially aligned passages 102, which may be two passages placed about 10 mm apart, are initially drilled through both of the patient's glenoid 104 and a graft, such as a bone graft 106. After the passages 102 are formed, the patient's shoulder 100 is prepared for insertion of the fixation device 10. Non-limiting examples of methods for preparing a patient's shoulder are described in U.S. Patent Publication No. 2014-0277185 (Boileau et al.), incorporated herein by reference. An ancillary fastener 40, such as a round button, may be pre-attached to a tension suture 28. Non-limiting examples of ancillary fasteners 40 are described in U.S. Patent Publication No. 2012/0310279 (Sikora et al.), U.S. Patent Publication No. 2014-0277185 (Boileau et al.), and in the Endobutton family of products (manufactured by Smith & Nephew, Inc., Andover, Mass., USA), incorporated herein by reference. The tension suture 28 is slidably passed through an opening 42 in the ancillary fastener 40, or otherwise coupled to the ancillary fastener 40, such that the distance between the ancillary fastener 40 and the fixation device 10 can be adjusted by pulling on the ends of the tension suture 28, as further described below. In FIG. 3A, the ends of the tension suture 28 are pulled, for example by shuttling suture (not shown), through the passages 102 in the patient's glenoid 104 and bone graft 106, until the ancillary fastener 40 is positioned below the glenoid 104 and the ends of the tension suture 28 extend from passages 102 in the bone graft 106.

As shown in FIG. 3B, with the ancillary fastener 40 positioned below the glenoid 104, the ends of the tension suture 28 are passed through the post 18 of fixation device 10 such that they exit the first surface 14 of the body 12. In one example, the diameter of the post 18 is selected to be substantially equal to the diameter of the passages 102, which may be about 2.8 mm. Since the passages 102 are formed through relatively soft, deformable bone, as the ends of the tension suture 28 are pulled, the fixation device 10 is reduced toward the bone graft 106 such that the post 18 is inserted into the passages 102, forming a slip fit with the passages 102. Once fully-inserted, the post 18 extends completely through the passages 102 of the bone graft 106 and at least partially through the passages 102 of the glenoid 104. As shown in FIG. 3C, once the bone graft 106 is in the preferred position, a surgical knot 32 is tied in the tension suture 28 above the first through hole 20 of the body 12, fixing the bone graft 106 into place. The ends of the tension suture 28 may then be trimmed.

Figure 4A:
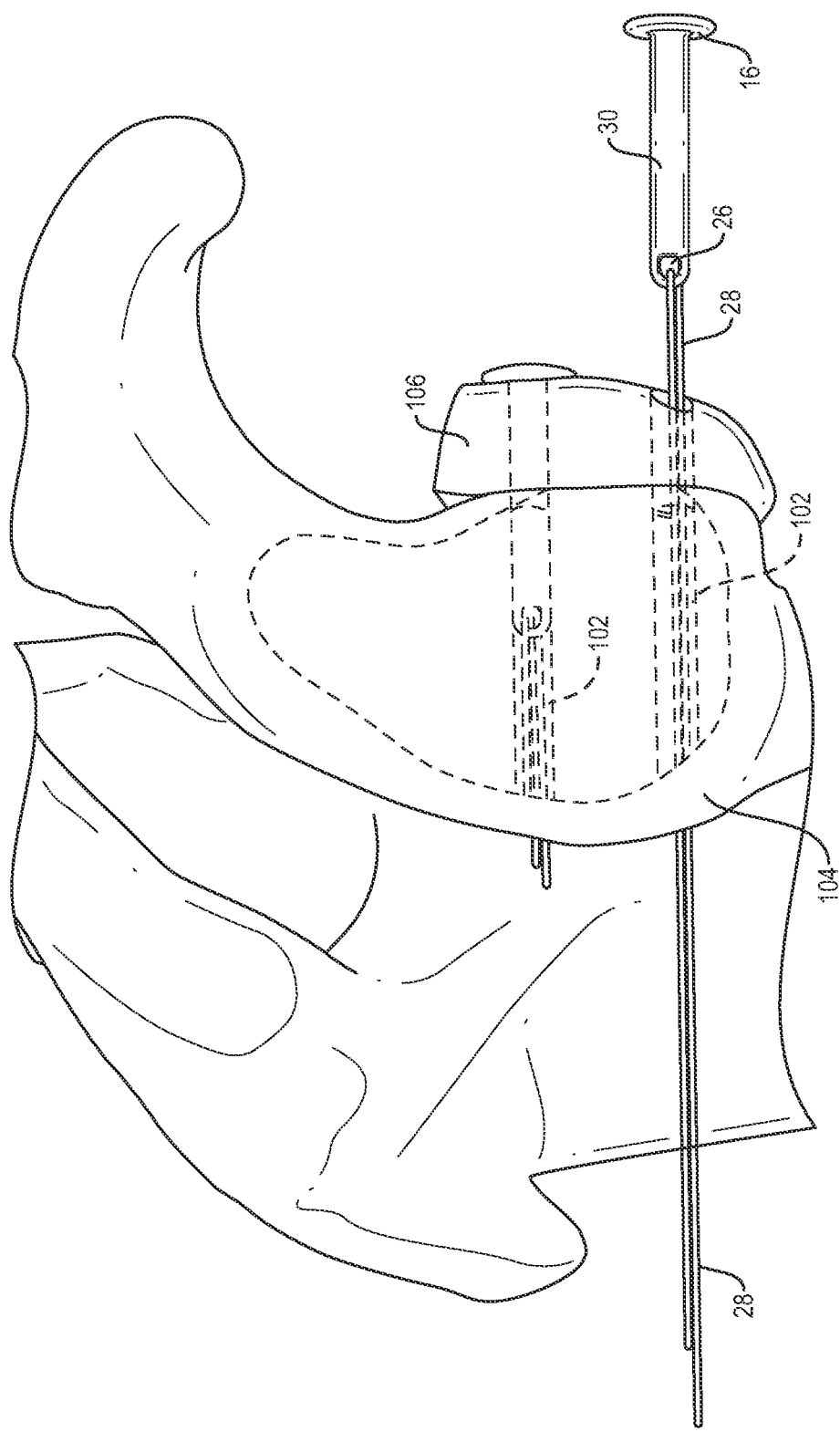
FIGS. 4A-C illustrate a method of graft fixation using the fixation device of FIGS. 2A and 2B.
Figure 4B:
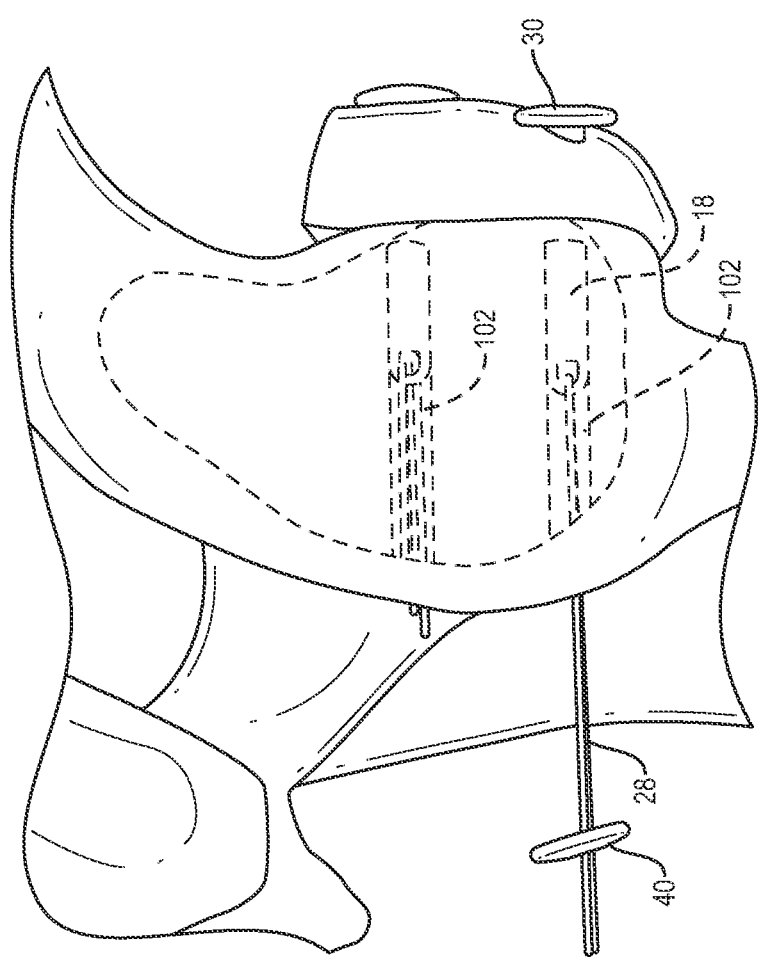
Figure 4C:
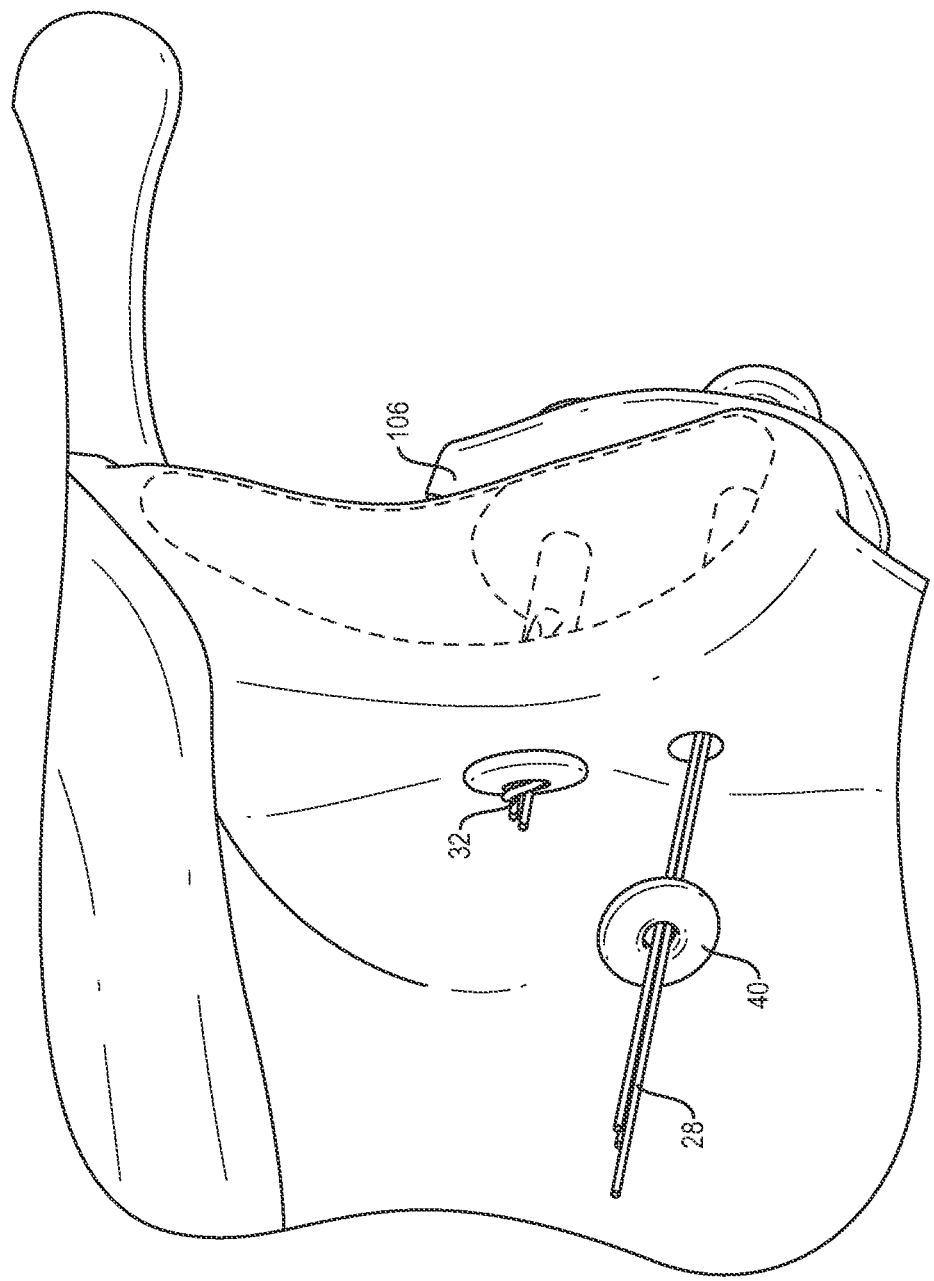
Figure 5A:
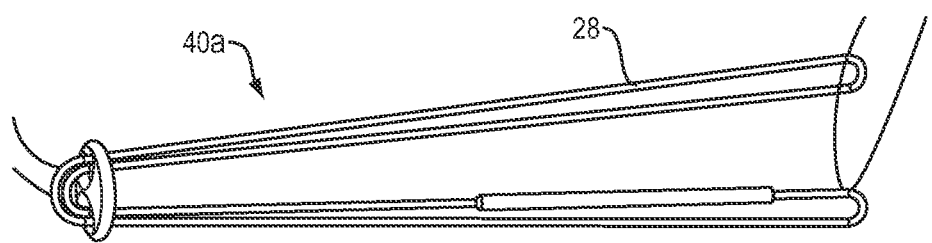
FIGS. 5A-E illustrate examples of an ancillary fastener to be used in the methods of graft fixation shown in FIGS. 3A-C and FIGS. 4A-C.
Figure 5B:
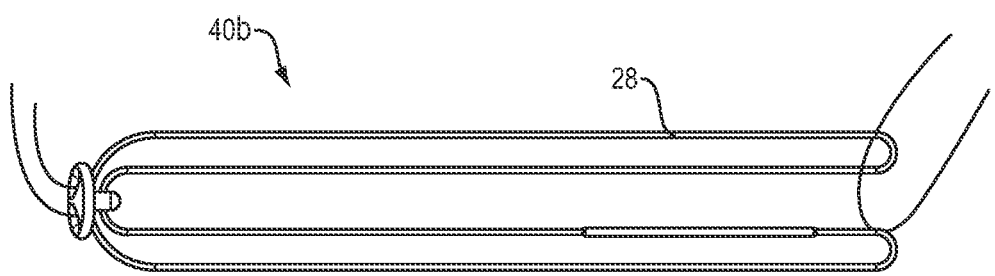
Figure 5C:
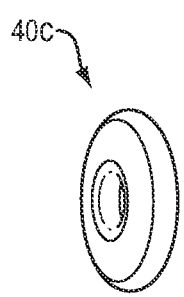
Figure 5D:
Figure 5E:
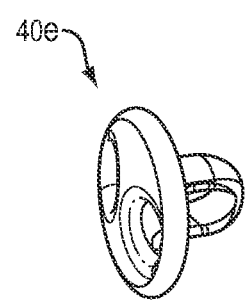

FIGS. 4A-C illustrate a method of bone graft fixation using fixation device 30 as described above. Referring to FIG. 4A, axially aligned passages 102 are drilled through the patient's glenoid 104 and a bone graft 106. A tension suture 28 is slidably coupled to the eyelet 26 of the fixation device 30 such that the distance between the fixation device 30 and an ancillary fastener 40 (FIG. 4B) can be adjusted by pulling on the ends of the tension suture 28. In FIG. 4A, the ends of the tension suture 28 are pulled through the passages 102 in the bone graft 106 and the patient's glenoid 104, until the second surface 16 of the fixation device 30 is positioned above the surface of the bone graft 106 and the ends of the tension suture 28 extend from passages 102 below the glenoid 104.

As shown in FIG. 4B, as the ends of the tension suture 28 are pulled, the fixation device 30 is reduced toward the bone graft 106 such that the post 18 is inserted into the passages 102. Once fully-inserted, the post 18 extends completely through the passages 102 of the bone graft 106 and at least partially through the passages 102 of the glenoid 104. The tension suture 28 is then coupled to an ancillary fastener 40. As shown in FIG. 4C, once the bone graft 106 is in the preferred position, a surgical knot 32 is tied in the tension suture 28 below the ancillary fastener 40, fixing the bone graft 106 into place. The ends of the tension suture 28 may then be trimmed.

Examples of ancillary fasteners 40 are illustrated in FIGS. 5A-E. Ancillary fasteners 40a and 40b (FIGS. 5A and 5B) comprise a device with a tension suture 28 pre-attached. Ancillary fastener 40a comprises two through holes in the device for passage of a suture, and ancillary fastener 40b additionally comprises a short, open post attached to the device for passage of a suture. Ancillary fasteners 40c-e (FIGS. 5C-E) comprise a device with one through hole (40c), two through holes (40d) or two through holes and a short, open post (40e) for passage of a suture. Either of the fixation devices 10, 30 may be coupled with the tension suture 28 as described above to one of the ancillary fasteners 40 shown in FIGS. 5A-E to form an enhanced tissue fixation construct. For example, fixation device 10 may be coupled to either of the ancillary fasteners 40a, 40b, and fixation device 30 may be coupled to one of the ancillary fasteners 40c, 40d, 40e, to form an enhanced tissue fixation construct.

One skilled in the art will realize the disclosure may be embodied in other specific forms without departing from the spirit or essential characteristics thereof. The foregoing examples are therefore to be considered in all respects illustrative rather than limiting of the disclosure described herein. Scope of the disclosure is thus indicated by the appended claims, rather than by the foregoing description, and all changes that come within the meaning and range of equivalency of the claims are therefore intended to be embraced therein.

What is claimed is:

1. A method of tissue graft fixation comprising:
    forming at least one axially aligned passage through a bone and a bone graft;
    passing a first portion of a suture through the at least one axially-aligned passage, a second portion of the suture being coupled to a first fastener;
    positioning the first fastener against a surface of one of the bone graft or the bone by pulling the second portion of the suture through the at least one axially-aligned passage until the second portion of the suture exits the at least one axially-aligned passage;
    positioning a second fastener against the other of the bone graft or the bone by coupling the second fastener to the second portion of the suture; and
    adjusting the suture such that the first fastener and the second fastener apply pressure between the bone graft and the bone;
    wherein one of the first fastener or the second fastener comprises:
        a generally flat, circular body having a first surface and a second surface opposite the first surface, the body defining a first through hole extending from the first surface to the second surface, the first through hole located near a center of the second surface; and
        a generally cylindrical post comprising a first end, a second end, and a longitudinal axis extending between the first and second ends, the longitudinal axis being perpendicular to the second surface of the body, the first end of the post being fixedly coupled to the center of the second surface, the post further defining a second through hole extending along the longitudinal axis from the first end to the second end, the second through hole in communication with the first through hole, the first and second through holes configured for passage of the suture; and
    wherein, when the suture is adjusted, the post extends through the at least one axially aligned passage such that it extends through the bone graft and at least partially through the bone.

2. The method of claim 1, wherein both of the first through hole and an outer surface of the post are non-threaded.

3. The method of claim 1, wherein a length of the post is between 20 mm and 25 mm.

4. The method of claim 1, wherein a diameter of the post is 2.8 mm.

5. The method of claim 1, wherein a diameter of the at least one axially aligned passage is 2.8 mm.

6. The method of claim 1, further comprising tying a surgical knot in the suture.

7. The method of claim 1, wherein the suture is slidably coupled to at least one of the first or second fasteners.

8. The method of claim 1, wherein the suture is in the form of a suture loop.

9. The method of claim 1, wherein the bone is a glenoid.

10. The method of claim 1, wherein the second fastener is different from the first fastener.

* * * * *